(12) United States Patent
Clausen et al.

(10) Patent No.: US 9,462,966 B2
(45) Date of Patent: *Oct. 11, 2016

(54) SENSING SYSTEMS AND METHODS FOR MONITORING GAIT DYNAMICS

(71) Applicant: Össur hf, Reykjavik (IS)

(72) Inventors: Arinbjörn Viggo Clausen, Reykjavik (IS); Magnús Oddsson, Hafnarfjordur (IS)

(73) Assignee: Össur hf, Reykjavik (IS)

( * ) Notice: Subject to any disclaimer, the term of this patent is extended or adjusted under 35 U.S.C. 154(b) by 86 days.

This patent is subject to a terminal disclaimer.

(21) Appl. No.: 14/522,247

(22) Filed: Oct. 23, 2014

(65) Prior Publication Data

US 2015/0105700 A1 Apr. 16, 2015

Related U.S. Application Data

(60) Continuation of application No. 13/405,039, filed on Feb. 24, 2012, now Pat. No. 8,869,626, which is a continuation of application No. 12/981,339, filed on Dec. 29, 2010, now Pat. No. 8,122,772, which is a division of application No. 11/346,600, filed on Feb. 2, 2006, now Pat. No. 7,867,285.

(60) Provisional application No. 60/649,226, filed on Feb. 2, 2005.

(51) Int. Cl.
*G01N 3/00* (2006.01)
*A61B 5/11* (2006.01)
(Continued)

(52) U.S. Cl.
CPC .............. *A61B 5/112* (2013.01); *A61B 5/1038* (2013.01); *A61F 2/66* (2013.01); *A61F 2/68* (2013.01); *A61F 2/76* (2013.01); *A61F 2002/5055* (2013.01); *A61F 2002/6614* (2013.01); *A61F 2002/6621* (2013.01); *A61F 2002/6642* (2013.01); *A61F 2002/6657* (2013.01);
(Continued)

(58) Field of Classification Search
CPC ................ A61B 5/1038; A61B 5/112; A61F 2002/6614; A61F 2002/7635
USPC ..................................................... 73/812, 760
See application file for complete search history.

(56) References Cited

U.S. PATENT DOCUMENTS 3,791,375 A 2/1974 Pfeiffer
3,820,168 A 6/1974 Horvath
(Continued)

FOREIGN PATENT DOCUMENTS

DE 42 29 330 3/1994
DE 19521464 6/1995
(Continued)

OTHER PUBLICATIONS

U.S. Appl. No. 13/354,188, filed Jan. 19, 2012, Bedard, et al.
(Continued)

*Primary Examiner* — Max Noori
(74) *Attorney, Agent, or Firm* — Knobbe, Martens, Olson & Bear, LLP

(57) ABSTRACT

Systems and method for monitoring gait dynamics are disclosed. The performance of an orthotic or prosthetic device or other device associated with a limb may be measured based on the resistance of a bending sensor. Data from the sensors is gathered or processed, particularly for purposes of alignment, safety, failure, usage, selection, and artificial proprioception. Information relating to the device may be outputted visually or auditorily to an individual.

20 Claims, 10 Drawing Sheets

(51) Int. Cl.
*A61B 5/103* (2006.01)
*A61F 2/66* (2006.01)
*A61F 2/68* (2006.01)
*A61F 2/76* (2006.01)
*A61F 2/50* (2006.01)
*A61F 2/70* (2006.01)
*A61F 5/01* (2006.01)

(52) U.S. Cl.
CPC ..... *A61F2002/6671* (2013.01); *A61F 2002/6685* (2013.01); *A61F 2002/704* (2013.01); *A61F 2002/705* (2013.01); *A61F 2002/769* (2013.01); *A61F 2002/7635* (2013.01); *A61F 2002/7645* (2013.01); *A61F 2002/7695* (2013.01); *A61F 2005/0188* (2013.01)

(56) References Cited

U.S. PATENT DOCUMENTS

| | | |
|---|---|---|
| 3,866,246 A | 2/1975 | Seamone et al. |
| 3,995,324 A | 12/1976 | Burch |
| 4,030,141 A | 6/1977 | Graupe |
| 4,179,759 A | 12/1979 | Smith |
| 4,209,860 A | 7/1980 | Graupe |
| 4,314,379 A | 2/1982 | Tanie |
| 4,387,472 A | 6/1983 | Wilson |
| 4,521,924 A | 6/1985 | Jacobsen et al. |
| 4,558,704 A | 12/1985 | Petrofsky |
| 4,770,662 A | 9/1988 | Giampapa |
| 4,808,187 A | 2/1989 | Patterson et al. |
| 4,814,661 A | 3/1989 | Ratzlaff et al. |
| 4,876,944 A | 10/1989 | Wilson et al. |
| 4,878,913 A | 11/1989 | Aebischer |
| 4,994,086 A | 2/1991 | Edwards |
| 5,033,291 A | 7/1991 | Podoloff et al. |
| 5,062,856 A | 11/1991 | Sawamura et al. |
| 5,062,857 A | 11/1991 | Barringer et al. |
| 5,086,785 A | 2/1992 | Gentile et al. |
| 5,133,773 A | 7/1992 | Sawamura et al. |
| 5,133,774 A | 7/1992 | Sawamura et al. |
| 5,200,679 A | 4/1993 | Graham |
| 5,219,365 A | 6/1993 | Sabolich |
| 5,252,102 A | 10/1993 | Singer et al. |
| 5,253,656 A | 10/1993 | Rincoe et al. |
| 5,269,081 A | 12/1993 | Gray |
| 5,299,454 A | 4/1994 | Fuglewicz |
| 5,323,650 A | 6/1994 | Fullen et al. |
| 5,336,269 A | 8/1994 | Smits |
| 5,357,696 A | 10/1994 | Gray et al. |
| 5,376,128 A | 12/1994 | Bozeman |
| 5,383,939 A | 1/1995 | James |
| 5,408,873 A | 4/1995 | Schmidt et al. |
| 5,413,611 A | 5/1995 | Haslam, II et al. |
| 5,443,524 A | 8/1995 | Sawamura et al. |
| 5,443,528 A | 8/1995 | Allen |
| 5,458,655 A | 10/1995 | Bozeman |
| 5,480,454 A | 1/1996 | Bozeman |
| 5,485,402 A | 1/1996 | Smith |
| 5,486,209 A | 1/1996 | Phillips |
| 5,563,458 A | 10/1996 | Ericson |
| 5,566,479 A | 10/1996 | Gray et al. |
| 5,571,205 A | 11/1996 | James |
| 5,571,213 A | 11/1996 | Allen |
| 5,583,476 A | 12/1996 | Langford |
| 5,642,096 A | 6/1997 | Leyerer et al. |
| 5,650,704 A | 7/1997 | Pratt et al. |
| 5,653,767 A | 8/1997 | Allen et al. |
| 5,678,448 A | 10/1997 | Fullen et al. |
| 5,695,527 A | 12/1997 | Allen |
| 5,704,946 A | 1/1998 | Greene |
| 5,725,598 A | 3/1998 | Phillips |
| 5,746,774 A | 5/1998 | Kramer et al. |
| 5,779,735 A | 7/1998 | Molino |
| 5,888,212 A | 3/1999 | Petrofsky et al. |
| 5,888,213 A | 3/1999 | Sears et al. |
| 5,888,246 A | 3/1999 | Gow |
| 5,893,891 A | 4/1999 | Zahedi |
| 5,895,430 A | 4/1999 | O'Connor |
| 5,929,332 A | 7/1999 | Brown |
| 6,006,412 A | 12/1999 | Bergmann et al. |
| 6,007,582 A | 12/1999 | May |
| 6,091,977 A | 7/2000 | Tarjan et al. |
| 6,113,642 A | 9/2000 | Petrofsky et al. |
| 6,129,766 A | 10/2000 | Johnson et al. |
| 6,195,921 B1 | 3/2001 | Truong |
| 6,342,076 B1 | 1/2002 | Lundborg |
| 6,361,570 B1 | 3/2002 | Gow |
| 6,423,098 B1 | 7/2002 | Biedermann |
| 6,425,925 B1 | 7/2002 | Grundei |
| 6,443,993 B1 | 9/2002 | Koniuk |
| 6,443,995 B1 | 9/2002 | Townsend et al. |
| 6,494,039 B2 | 12/2002 | Pratt et al. |
| 6,500,210 B1 | 12/2002 | Sabolich et al. |
| 6,517,503 B1 | 2/2003 | Naft et al. |
| 6,517,585 B1 | 2/2003 | Zahedi et al. |
| 6,537,322 B1 | 3/2003 | Johnson et al. |
| 6,589,287 B2 | 7/2003 | Lundborg |
| 6,610,101 B2 | 8/2003 | Herr et al. |
| 6,679,920 B2 | 1/2004 | Biedermann et al. |
| 6,695,885 B2 | 2/2004 | Schulman et al. |
| 6,719,806 B1 | 4/2004 | Zahedi et al. |
| 6,740,123 B2 | 5/2004 | Davalli et al. |
| 6,755,870 B1 | 6/2004 | Biedermann et al. |
| 6,764,520 B2 | 7/2004 | Deffenbaugh et al. |
| 6,770,045 B2 | 8/2004 | Naft et al. |
| 6,811,571 B1 | 11/2004 | Phillips |
| 6,918,308 B2 | 7/2005 | Biedermann |
| 6,955,692 B2 | 10/2005 | Grundei |
| 7,029,500 B2 | 4/2006 | Martin |
| 7,137,998 B2 | 11/2006 | Bedard |
| 7,147,667 B2 | 12/2006 | Bedard |
| 7,279,009 B2 | 10/2007 | Herr et al. |
| 7,314,490 B2 | 1/2008 | Bedard et al. |
| 7,377,944 B2 | 5/2008 | Janusson et al. |
| 7,410,471 B1 | 8/2008 | Campbell et al. |
| 7,431,737 B2 | 10/2008 | Ragnarsdottir et al. |
| 7,611,543 B2 | 11/2009 | Townsend et al. |
| 7,736,394 B2 | 6/2010 | Bedard et al. |
| 7,780,741 B2 | 8/2010 | Janusson et al. |
| 7,794,505 B2 | 9/2010 | Clausen et al. |
| 7,799,091 B2 | 9/2010 | Herr et al. |
| 7,811,334 B2 | 10/2010 | Ragnarsdottir et al. |
| 7,815,689 B2 | 10/2010 | Bedard et al. |
| 7,862,620 B2 | 1/2011 | Clausen et al. |
| 7,867,284 B2 | 1/2011 | Bedard |
| 7,867,285 B2 | 1/2011 | Clausen et al. |
| 7,927,338 B2 * | 4/2011 | Laffargue ............ A61F 2/4657 600/595 |
| 7,955,398 B2 | 6/2011 | Bedard et al. |
| 8,122,772 B2 * | 2/2012 | Clausen ............... A61B 5/1038 73/760 |
| 8,869,626 B2 * | 10/2014 | Clausen ........................ 73/812 |
| 2001/0020143 A1 | 9/2001 | Stark et al. |
| 2001/0029400 A1 | 10/2001 | Deffenbaugh et al. |
| 2002/0052663 A1 | 5/2002 | Herr et al. |
| 2002/0103543 A1 | 8/2002 | Asai |
| 2002/0138153 A1 | 9/2002 | Koniuk |
| 2002/0183803 A1 | 12/2002 | Fang et al. |
| 2003/0120353 A1 | 6/2003 | Christensen |
| 2004/0049290 A1 | 3/2004 | Bedard |
| 2004/0054423 A1 | 3/2004 | Martin |
| 2004/0059432 A1 | 3/2004 | Janusson et al. |
| 2004/0064195 A1 | 4/2004 | Herr |
| 2004/0088057 A1 | 5/2004 | Bedard |
| 2004/0181289 A1 | 9/2004 | Bedard et al. |
| 2004/0193286 A1 | 9/2004 | Grundei |
| 2004/0267379 A1 | 12/2004 | Pasolini |
| 2005/0029979 A1 | 2/2005 | Lee et al. |
| 2005/0107889 A1 | 5/2005 | Bedard et al. |
| 2005/0131317 A1 | 6/2005 | Oddsson et al. |
| 2005/0192677 A1 | 9/2005 | Ragnarsdottir et al. |
| 2005/0197717 A1 | 9/2005 | Ragnarsdottir et al. |
| 2005/0234562 A1 | 10/2005 | Okuda et al. |
| 2005/0283257 A1 | 12/2005 | Bisbee et al. |

(56) References Cited

U.S. PATENT DOCUMENTS

| | | |
|---|---|---|
| 2006/0122711 A1 | 6/2006 | Bedard et al. |
| 2006/0135883 A1 | 6/2006 | Jonsson et al. |
| 2006/0136072 A1 | 6/2006 | Bisbee et al. |
| 2006/0173552 A1 | 8/2006 | Roy |
| 2006/0184252 A1 | 8/2006 | Oddsson et al. |
| 2006/0184280 A1 | 8/2006 | Oddsson et al. |
| 2006/0224247 A1 | 10/2006 | Clausen et al. |
| 2006/0249315 A1 | 11/2006 | Herr et al. |
| 2007/0016329 A1 | 1/2007 | Herr et al. |
| 2007/0043449 A1 | 2/2007 | Herr et al. |
| 2007/0123997 A1 | 5/2007 | Herr et al. |
| 2007/0162152 A1 | 7/2007 | Herr et al. |
| 2008/0046096 A1 | 2/2008 | Bedard et al. |
| 2008/0139959 A1* | 6/2008 | Miethke ............... A61B 5/0031 600/561 |
| 2008/0288086 A1 | 11/2008 | Auberger et al. |
| 2010/0063778 A1 | 3/2010 | Schrock et al. |
| 2010/0185124 A1 | 7/2010 | Bisbee et al. |
| 2010/0262260 A1 | 10/2010 | Bedard et al. |
| 2011/0130847 A1 | 6/2011 | Bedard et al. |

FOREIGN PATENT DOCUMENTS

| | | |
|---|---|---|
| EP | 0 549 855 | 7/1993 |
| EP | 1 166 726 | 1/2002 |
| EP | 1169982 A1 | 1/2002 |
| EP | 1843724 | 10/2007 |
| FR | 2293185 | 7/1976 |
| FR | 2623086 | 5/1989 |
| GB | 2201260 | 8/1988 |
| GB | 2 260 495 | 4/1993 |
| GB | 2 302 949 | 2/1997 |
| JP | 11056885 | 3/1999 |
| JP | 2001-277175 | 10/2001 |
| JP | 2002-191654 | 7/2002 |
| KR | 2002-0041137 | 6/2002 |
| WO | WO 96/41599 A | 12/1996 |
| WO | WO 98/25552 | 6/1998 |
| WO | WO 99/08621 | 2/1999 |
| WO | WO 99/29272 | 6/1999 |
| WO | WO 00/38599 A1 | 7/2000 |
| WO | WO 01/72245 | 10/2001 |
| WO | WO 2004/017871 A2 | 3/2004 |

OTHER PUBLICATIONS

Chinese Office Action dated Oct. 30, 2009 in application No. 200680010926.2, filed Feb. 1, 2006.
Corrected PCT International Search Report and Written Opinion, dated Mar. 5, 2007 in PCT/US2006/003473.
Dietl, H., Der Einsatz von Elektronik bei Prothesen zur Versorgung der unteren Extremitat, Med. Orth. Tech. 117 (1997) pp. 31-35.
European Office Action dated Dec. 6, 2010.
European Office Action dated Mar. 4, 2009.
Fernando, Gerard F., "Fibre optic sensor systems for monitoring composite structures," RP Asia 2005 conference in Bangkok, Aug. 25/26, 2005. The University of Birmingham, Edgbaston, Birmingham, UK.
Flowers et al., Journal of Biomedical Engineering: Transactions of the ASME; Feb. 1977, pp. 3-8.
http://www.spectrasymbol.com/howitworks.html, Sep. 8, 2006.
http://www.spectrasymbol.com/medical.html, Sep. 8, 2006.
Otto Bock, "The Electronic C-Leg® Knee Joint System: Instructions for Use," available at http://www.ottobockus.com/products/lower_limp_prosthetics/c-leg_instructions.pdf, 32 pages, Published 2002, Printed in Germany, 647H-215=GB, 07.02/1-Internet.
PCT International Search Report and Written Opinion, dated Nov. 24, 2006 in PCT/US2006/003473.
May 25, 2011 Search Opinion and Search Report for European Application No. 11156688 filed Feb. 1, 2006.
Nov. 22, 2011 Office Action for Chinese Application No. 200680010926.2 filed on Feb. 1, 2006.
Jun. 13, 2012 Office Action for Canadian Patent Application No. 2,595,895 filed on Feb. 1, 2006.
Apr. 4, 2013 European Office Action for Application No. 06 748 179.6 filed on Feb. 1, 2006.
Aug. 22, 2013 Canadian Office Action for Application No. 2595895 filed on Feb. 1, 2006.
Apr. 24, 2014 Canadian Office Action for Application No. 2595895 filed on Feb. 1, 2006.
Nov. 27, 2014 Canadian Office Action for Application No. 2595895 filed on Feb. 1, 2006.

* cited by examiner

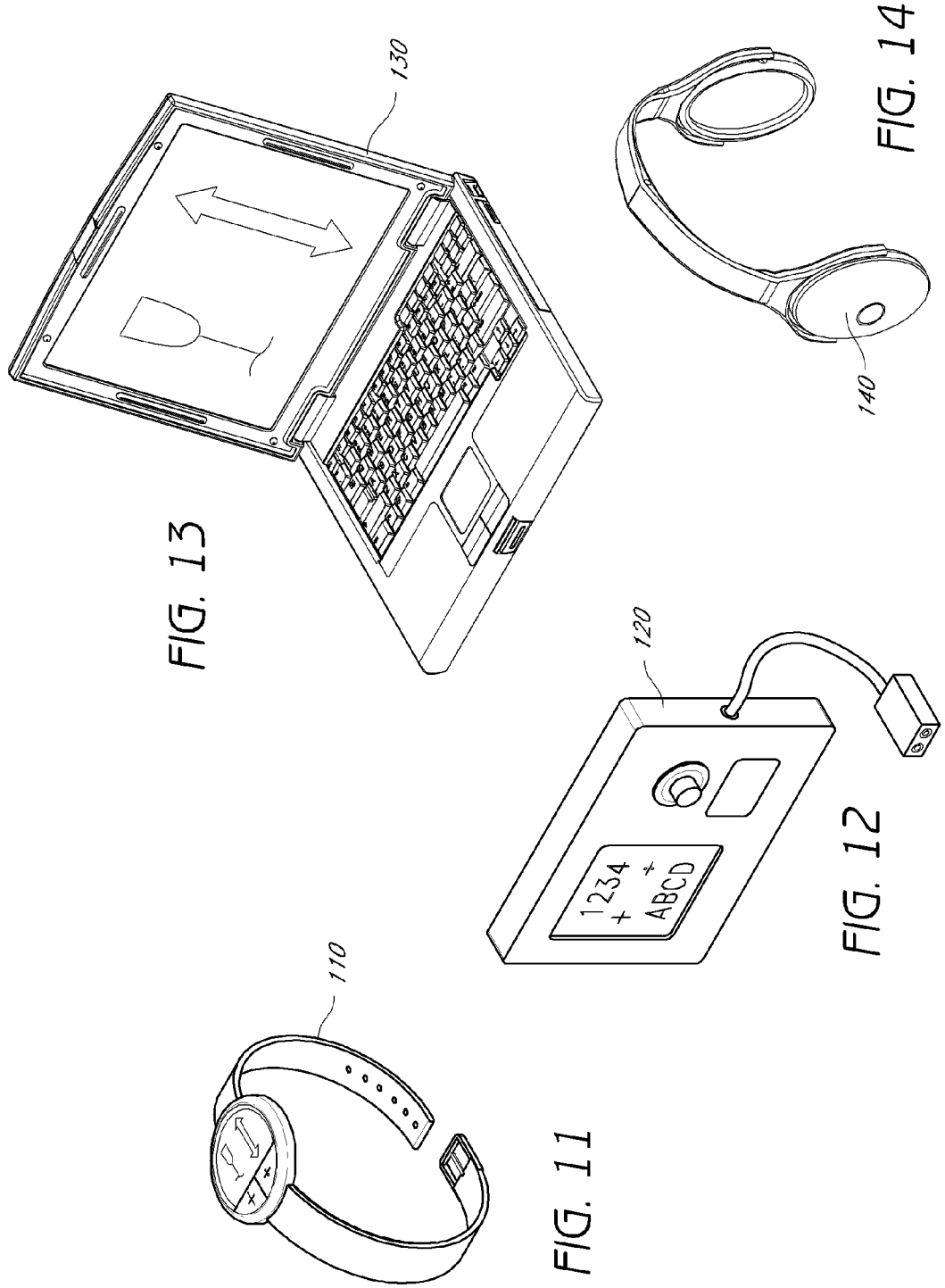

SENSING SYSTEMS AND METHODS FOR MONITORING GAIT DYNAMICS

CROSS-REFERENCE TO RELATED APPLICATION

This application is a continuation application of U.S. application Ser. No. 13/405,039 entitled SENSING SYSTEMS AND METHODS FOR MONITORING GAIT DYNAMICS" filed on Feb. 24, 2012, which is a continuation application of U.S. application Ser. No. 12/981,339, entitled "SENSING SYSTEMS AND METHODS FOR MONITORING GAIT DYNAMICS," filed on Dec. 29, 2010, now U.S. Pat. No. 8,122,772, which is a divisional application of U.S. application Ser. No. 11/346,600, entitled "SENSING SYSTEMS AND METHODS FOR MONITORING GAIT DYNAMICS," filed on Feb. 2, 2006, now U.S. Pat. No. 7,867,285, which claims priority to U.S. Provisional Patent Application No. 60/649,226, filed on Feb. 2, 2005, the entirety of all of which are hereby incorporated by reference.

BACKGROUND OF THE INVENTION

1. Field of the Invention

Embodiments of the invention relate to sensing systems and methods and, in particular, sensors for use in monitoring the gait dynamics of a user.

2. Description of the Related Art

Millions of individuals worldwide rely on prosthetic and/or orthotic devices to compensate for disabilities, such as amputation or debilitation, and to assist in the rehabilitation of injured limbs. Orthotic devices include external apparatuses used to support, align, prevent, protect, correct deformities of, or improve the function of movable parts of the body. Prosthetic devices include apparatuses used as artificial substitutes for a missing body part, such as an arm or leg. The number of disabled persons or amputees is increasing each year as the average age of individuals increases, as does the prevalence of debilitating diseases such as diabetes. As a result, the need for prosthetic and orthotic devices is also increasing.

In order to improve operability, prosthetic and orthotic devices may be properly aligned by a trained professional, such as a licensed prosthetist. One conventional means for correctly aligning a prosthetic/orthotic device employs laser beams to determine the center of gravity of a device while being worn. Unfortunately, the use of this alignment method requires expensive equipment that is not very portable. Hence, there is a need for technology to align prosthetic/orthotic devices that is both affordable and portable. Such a technology would also be valuable for other industries that manufacture devices associated with limbs, such as clothing and sporting-equipment industries, which also lack an affordable and portable technology for properly aligning devices, such as shoes, ski boots, etc.

Some prosthetic/orthotic devices employ sensors to gather data relevant to the device. One relevant source of information is the amount of pressure placed on a prosthetic/orthotic device, such as a prosthetic foot, while walking. Unfortunately, a single conventional sensor attached to a prosthetic foot, generally, only detects either a heel strike or a toe load. Conventional sensors, generally, cannot be positioned on a prosthetic foot to measure both a heel strike and a toe load. Hence, there is a need for improved sensors for prosthetic/orthotic devices. Such a sensor technology would also be valuable for other industries that manufacture devices associated with limbs, such as clothing and sporting-equipment industries, which also lack sensors capable of being positioned on a device associated with a foot in such a way that allows for the detection of both a heel strike and toe load while walking, running, etc.

Some prosthetic/orthotic devices have sensor systems that interact with the device, causing the device to automatically adjust itself based on sensor readings. Unfortunately, conventional sensor systems do not provide efficient, cost-effective technologies for storing cumulative information regarding, for instance, a user's gait dynamics. Hence, there is a need for prosthetic/orthotic devices that store cumulative performance characteristics of the respective device. Such technology may also be valuable for other industries that manufacture devices associated with limbs.

Some prosthetic/orthotic devices provide sensory feedback to the user. One disadvantage of conventional sensory feedback systems, however, is that they involve electrical stimulus. Among other potential problems, these systems may be (or at least may appear to be) uncomfortable, unaesthetic, and unsafe. Hence, there is a need for improved sensory feedback systems. Improved sensory feedback systems may also be valuable for other industries that manufacture devices associated with limbs.

Currently, there are sensors that measure the surface strain of a material. For instance, it is commonly known to use strain gauges to measure the actual strain in the surface of a material. These strain gauges may measure the changes in electrical resistance as certain strained forces are applied to the material. As the strain gauges are attached to a material surface, the strain gauges typically measure only the strain at the material surface. There are many disadvantages to using strain gauges. For instance, conventional strain gauges do not isolate the change in resistance due to the deformations in surface to which the sensor is attached. Thus, temperature, material properties, the adhesive that bonds the gauge to the surface, and the stability of the material all affect the detected resistance. For example, in the prosthetics industry, individual prosthetic devices, such as a prosthetic foot, may be made from a variety of materials. Thus, conventional strain gauges would have to be calibrated for every foot made of a different material. Additionally, it may even be necessary to calibrate different foot devices of the same material. This unit-per-unit calibration is expensive and impractical. Another limitation of conventional stain gauges is that they are not flexible enough for certain applications, such as attachment to prosthetic feet. Conventional strain gauges measure a miniscule range of surface tension. Very flexible materials, such as carbon fiber used for prosthetic feet, exceed this range. Adapting conventional strain gauges for use with flexible devices associated with a limb, such as a prosthetic foot, may be impractical and expensive and may have an undesirable affect on the functionality of the device. Thus, there is a need for improved sensors for devices associated with a limb, such as a prosthetic foot.

No attempt is made here to catalogue all of the needs in the prior art to which embodiments of the invention are directed. It will be appreciated by one skilled in the art that the embodiments described below are directed to solving the needs mentioned above, as well as other needs not listed.

SUMMARY OF THE INVENTION

Certain embodiments of the invention relate to systems and methods for monitoring gait dynamics. In one embodiment, an intelligent foot employs a flexible sensor along a portion of the foot to measure the bending of the foot. Based on certain ranges, the data collected from the sensor (or sensors) may be used, for instance, by a trained prosthetist to detect the occurrence or pattern of successive heel strikes and/or toe loads on the prosthetic foot. This data may be used, for example, to align (either statically or dynamically) or to select an appropriate prosthetic foot. In addition, it may also be used to predict and to prevent potential failure of the device, as well as other potential safety hazards. Moreover, it may further be used to train users of prosthetic devices to recognize and to associate the detected gait dynamics with the associated pressures caused by the wearing of the device. Although the attached drawings and the description below often describe the invention in terms of a prosthetic foot, the invention is not limited to this application. Embodiments of the invention may include applications to many different prosthetic and orthotic devices, such as, but not limited to, torsos, arms, necks, legs, hands, etc. Additionally, embodiments of the invention may include applications to other devices associated with limbs, such as, for instance, clothing articles (e.g., shoes) and sporting goods equipment (e.g., ski boots).

One embodiment of the invention includes a system for measuring performance of an orthotic or prosthetic device, comprising an orthotic or prosthetic device, the device capable of bending while in use, and a sensor, wherein the sensor is configured to bend with the device while in use, and wherein the sensor produces a resistance output correlated to the bending of the device. Another embodiment of the invention includes a method for measuring bending of an orthotic or prosthetic device associated with a limb, comprising providing an orthotic or prosthetic device having at least one sensor associated therewith, measuring with said sensor the bending of the sensor while the device is in use, said sensor bending with the device, and communicating information regarding said bending. Another embodiment of the invention includes a system for measuring performance of a device associated with a lower limb, comprising a device associated with a lower limb, the device capable of bending while in use, and a sensor, wherein the sensor is configured to bend with the device while in use, and wherein the sensor produces a resistance output correlated to the bending of the device. Yet another embodiment includes a prosthetic foot system, comprising a prosthetic foot, at least one sensor comprising a resistive strip provided along a portion of the prosthetic foot, the resistive strip configured to bend with the prosthetic foot while the foot is in use, and means for communicating bending information measured by said sensor to an individual.

One embodiment of the invention includes a method of gathering information regarding a prosthetic foot, comprising providing a prosthetic foot having at least one sensor associated therewith, measuring with said sensor a performance characteristic of said device while in use, and storing data corresponding to performance characteristics measured by said sensor within a memory. Another embodiment of the invention includes a method of gathering information regarding a device associated with a limb, comprising providing a device associated with a limb having at least one sensor associated therewith, measuring with said sensor a toe load value and heel strike value of said device while in use, and determining whether the at least one of said toe load value and heel strike value falls within a predetermined range indicative of different states of a user's gait. Another embodiment of the invention includes a method for assessing whether a device associated with a limb is in a suitable working condition, comprising providing a device associated with a limb having at least one sensor associated therewith, measuring with said sensor a biomechanical characteristic of said device while in use, communicating information from said sensor to a processor, and processing said information to determine whether said device is or is not in a suitable working condition, and providing a signal indicating whether said device is or is not in a suitable working condition. Another embodiment of the invention includes a device for attachment to a limb, comprising at least one sensor associated with the device configured to measure biomechanical characteristic of said device while in use, a processor configured to process information selected from the sensor to determine whether said device satisfies a desired condition selected from the group consisting of: alignment, safety, and failure, and a user interface indicating whether said device satisfies the condition. Yet another embodiment includes a prosthetic foot system, comprising a prosthetic foot, at least one sensor provided on the prosthetic foot configured to measure a performance characteristic of said foot while in use, and a memory storing information gathered by said sensor to compile a history of the performance characteristic of said foot while in use.

One embodiment of the invention includes a method of providing information regarding a prosthetic foot, comprising providing a prosthetic foot having at least one sensor associated therewith, measuring with said sensor a force characteristic of said device while in use, and outputting to an individual information auditorily or visually corresponding to the force characteristic. Another embodiment of the invention includes a system for measuring performance of a prosthetic foot, comprising a prosthetic foot, a sensor on the device configured to measure a force characteristic of the device, and a user interface providing audio or visual information relating to the force characteristic measured. Another embodiment of the invention includes a method of providing information to a user of a device associated with a limb, comprising providing a device associated with a limb having at least one sensor associated therewith, measuring with said sensor a load characteristic of said device while in use, and transmitting information relating to the load characteristic to the user of the device through sound.

One embodiment of the invention includes a method of determining activity of a device associated with a limb of a user. The method comprises in one embodiment: calculating a step factor based on the number of steps taken by the user over a period of time using at least one sensor provided on the device; calculating an impact level factor of the device using the at least one sensor, the impact level being determined by measuring a toe load and/or heel load of the user over the time period and comparing the measured toe or heel load to a predetermined threshold value (e.g., threshold toe load or threshold heel load) to determine if the threshold value is exceeded; and determining an activity index value for the user based on the step factor and the impact level factor.

For example, in one embodiment, the method may include calculating the number of times during a particular cycle that the measured load exceeds the predetermined threshold.

In yet other embodiments, an absolute value indicative of the measured toe load and/or heel load is used to determine the activity index value. For example, the method for determining activity of the user may comprise determining a toe load value and a heel load value for each step of the user. This load value data is then processed to determine a momentum value for the particular user. For instance, such processing may include filtering the load value data, such as through a low pass filter, and/or assigning the data weighted values. The method further includes extracting a weight component and an activity component from the determined momentum value. For instance, the weight of the user maybe acquired through the use of an external scale, the user profile data, and/or the sensors that measure a force value when both the toe and heel of the user are in contact with the ground. The remaining activity component is then used to determine the activity index of the user.

For example, in one embodiment, an algorithm for calculating the activity index of the user is as follows. A weight factor ("W") is calculated through the following equation:

$$W_n = (1-a)*\text{ToeLoadmax}_n + a*\text{HeelLoadmax}_n;$$

where "n" represents the step number; "ToeLoadmax" represents the maximum measured toe load; "HeelLoadmax" represents the maximum measured heel load; and where "a" is a variable representing the relationship between the ToeLoadmax and the HeelLoadmax measurements. This data is then filtered, such as through the following equation:

$$Wf_n = (1-b)*Wf_{n-1} + b*W_n$$

where b may be a constant variable, such as 0.05 (wherein the last monitored step only accounts for 5% of the total Wfn). The activity index ("A") may then be calculated by:

$$A = Wf/(\text{weight of user in kilograms})$$

Because the weight of the user does not generally change during the calculation process, then an increase in "A" can be attributed to an increase in Wf, which represents a more dynamic pattern of motion. It should also be recognized that the ToeLoadmax and HeelLoadmax variables may be set to zero during initialization of the calculation process. Furthermore, in other embodiments, the measurements of the toe load and/or heel load may comprise measurements other than the maximum load measurements. For example, the measurements of the toe load and/or heel load may comprise an average measurement during the length of one stride.

In one embodiment, the device may comprise an orthotic device or a prosthetic device, such as, for example, a prosthetic foot, or any of the devices described in the applications incorporated by reference herein.

In a further embodiment, the method includes comparing the activity index value for the user against a pre-determined activity index for a variety of different devices to select an appropriate device for the user.

One embodiment of the invention includes a method of selecting a device associated with a limb of a user. The selection method of one embodiment includes: providing a device having a sensor secured thereto; measuring with the sensor a performance characteristic of the device while the device is in use by a user; comparing the performance with a pre-determined matrix of performance data of different devices; and selecting an appropriate device for the user based on the comparison.

In one embodiment, the device may comprise an orthotic device or a prosthetic device, such as, for example, a prosthetic foot, or any of the devices described in the applications incorporated by reference herein. In further embodiments, the sensor may be configured to measure a toe and/or a heel load.

One embodiment of the invention includes a method of aligning a device associated with a limb of a user. The method of one embodiment includes: providing a device having at least one sensor secured thereto; measuring with the sensor a performance characteristic of the device while the device is in use by a user; transmitting data from the sensor to a microprocessor and processing the data; and aligning the device based on the data.

In one embodiment, the device may comprise an orthotic device or a prosthetic device, such as, for example, a prosthetic foot, or any of the devices described in the applications incorporated by reference above. In further embodiments, the sensor may measure load characteristics of the limb and/or device.

In one embodiment, such alignment may include anterior and/or posterior alignment of the device, such as through manual and/or automatic adjustments. In other embodiments, alignment may comprise adjustments for medial/lateral movement. For example, a plurality of resistive strips placed on both sides of a foot device may be used to determine toe load, heel load, foot moment, and/or movement in the medial/lateral plane.

In further embodiments, the method may additionally comprise at least one of the following: providing real-time alignment information during adjustment; providing information regarding alignment, activity, step count, combinations of the same, or the like through a computer interface; providing information on how a specific device has been treated; and/or providing recommendations on device choice based on measurements.

In yet other embodiments, information gathered from the sensors may be used to electronically and/or automatically adjust the device. For example, sensor signals could be used to trigger a release point in a knee-type device or to communicate with an associated neuromusculoskeletal (NMS) unit.

One embodiment of the invention includes a method of measuring bending of a device associated with a limb of a user. The method of one embodiment comprises providing a device having at least one sensor secured thereto; and measuring a bending characteristic of the device using the sensor as the limb is utilized by a user. For example, the method may be used to measure and/or detect large deflections/bending of materials, such as for example, carbon and other highly flexible materials used with the device. In one embodiment, the device may comprise an orthotic device or a prosthetic device, such as, for example, a prosthetic foot, or any of the devices described in the applications incorporated by reference above. In a further embodiment, multiple sensors measure the bending characteristics and/or load characteristics of a prosthetic foot. For example, one resistive strip sensor may be placed on each side of the prosthetic foot.

One embodiment of the invention includes a system for measuring prosthetic or orthotic performance. In one embodiment, the system includes a prosthetic foot and a sensor, such as, for example, a resistive strip, secured to the prosthetic foot. In another embodiment, the system includes a prosthetic foot and a sensor secured to the prosthetic foot configured to measure a bending characteristic of the foot over a designated step cycle. In yet another embodiment, the system includes a prosthetic foot, a sensor secured to the prosthetic foot; and a display secured to the prosthetic foot to indicate performance based on the measurements taken by the sensor.

Furthermore, each of the sensors may be laminated into the prosthetic foot, such as, for example, being laminated between layers of fibers.

BRIEF DESCRIPTION OF THE DRAWINGS

FIG. 11 illustrates a watch interface that may be used to display data gathered from the sensors of an intelligent device.

FIG. 12 illustrates a personal computing device that may be used to display data gathered from the sensors of an intelligent device.

FIG. 13 illustrates a laptop that may be used to display the data gathered from the sensors of an intelligent device.

FIG. 14 illustrates a set of headphones that may be used to hear the data gathered from the sensors of an intelligent device.

DETAILED DESCRIPTION OF THE PREFERRED EMBODIMENTS

Figure 1:
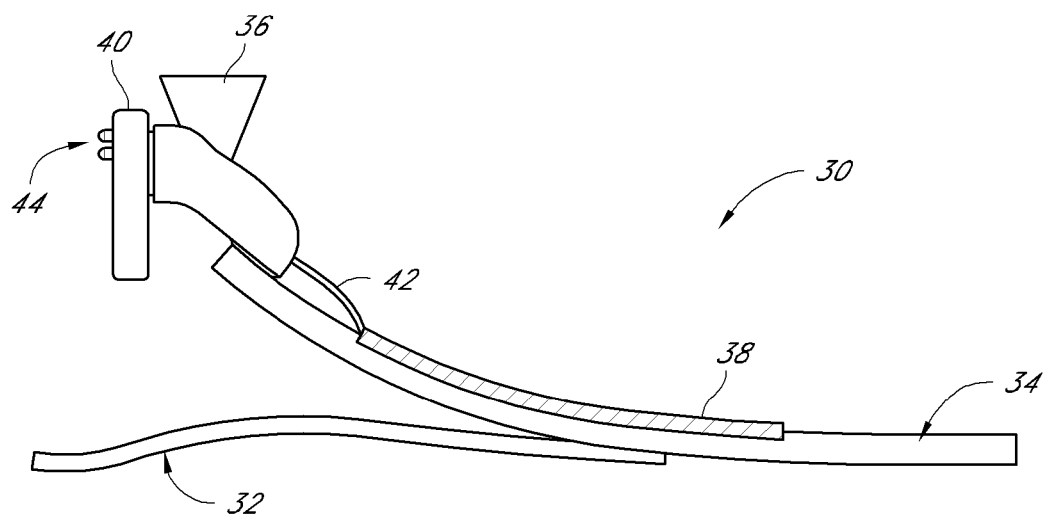
FIG. 1 illustrates a side view of an intelligent prosthetic foot with a single sensor.

Without limitation to the scope of the invention, certain inventive embodiments are described below. Various aspects and features of the invention will become more fully apparent from the following description and appended claims taken in conjunction with the foregoing drawings. In the drawings, like reference numerals indicate identical or functionally similar elements. The drawings, associated descriptions, and specific implementation are provided to illustrate the embodiments of the invention and not to limit the scope of the disclosure.

The terms "prosthetic" and "prosthesis" as used herein are broad terms and are used in their ordinary sense and refer to, without limitation, any system, device or apparatus that may be used as an artificial substitute or support for a body part.

The term "orthotic" and "orthosis" as used herein are broad terms and are used in their ordinary sense and refer to, without limitation, any system, device or apparatus that may be used to support, align, prevent, protect, correct deformities of, immobilize, or improve the function of parts of the body, such as joints and/or limbs.

The term "auditorily" as used herein means, without limitation, relating to or experienced through hearing. For instance, outputting to an individual information auditorily might mean transmitting sound waves to a pair of headphones via wired or wireless communication.

The phrase "transmitting information through sound" comprises any means of communicating information through sound waves perceptible to the human ear.

The term "alignment" as used herein means, without limitation, configuring the movable portions of a device so that the device functions properly or optimally. For instance, a trained prosthetist might use an intelligent device to adjust the alignment of, for instance, a prosthetic foot to a user. The alignment might be part of the initial fitting of the prosthetic or a later adjustment. Alignment may be as simple as tightening, or otherwise adjusting, screws, bolts, etc. By defining alignment as configuring movable parts, there is no intention to limit alignment to the adjustment of rotating, sliding, or other adjustments that require repositioning. The tightening of a bolt, for instance, should be construed as the configuration of a movable part. Alignment may include any configurable axis of device. For instance, a prosthetic foot may be aligned by adjusting the heel height. Alternatively, a prosthetic foot may be adjusted by aligning the lateral position of the foot to the user's stump. Alternatively, alignment may include the movement of a prosthetic foot in the heel-to-toe axis or forward and backward axis. Alignment may refer to either static or dynamic alignment. When the term "alignment" is used without either of the adjectives, it should be understood that the alignment refers to static and/or dynamic alignment. Static alignment, generally, occurs while the user of a device associated with a limb is in a still position, perhaps standing, sitting, or lying down. Dynamic alignment, on the other hand, is alignment based on measurements that represent user dynamics during gait, either normal level ground gait or more complex situations. In general, the term "alignment" is used both to indicate the actual adjustment of the intelligent device by the movement of parts and to indicate the analysis or process of determining how to configure the movable parts.

A device associated with a limb is any device that may be used to assist the limb in some function. For instance, a prosthetic device is a device associated with a limb. A prosthetic device may replace a portion of or the entire limb. Alternatively, an orthotic device is a device associated with a limb. An orthotic device, for instance, supports or aligns the limb. Additionally, other devices, such as articles of clothing or sporting goods equipment, may be devices associated with a limb. For instance, a shoe is a device associated with a limb because it assists the user of the shoe to use the foot, for example, to walk or run. Similarly, a ski boot is a device associated with a limb because it assists the user of the ski boot to use the foot, for example, to ski.

A bending force sensor is a sensor that measures bending force. One example of a bending force sensor is a variable printed resistor on a thin flexible substrate. As the substrate is bent, the sensor produces a resistance output correlated to the bend radius. That is, the smaller the radius, the higher the resistance value. Thus, a bending force sensor may be a sensor that bends.

A force characteristic of a device is any characteristic indicative of a force associated with the device. The force may be an external force, such as pressure applied to the device, for instance, when a prosthetic foot makes contact with the ground while a user is walking. A force may also be an internal force, such as the resistance of a conductive material with which the device is comprised. A force characteristic may be derived from other measurements and may form the basis for other derived measurements. For instance, a force characteristic may be the amount of bending experienced by a component of the device. This measured bending may be determined, for instance, by measuring the resistance of the component. Moreover, the measured bending, or resistance, may be used to measure whether the user of the device, such as a prosthetic foot, has entered a certain state of use, such as a heel strike state in the gait of the device user.

The phrase "suitable working condition" as used herein is intended to indicate a number of conditions relating to the proper and optimal use of a device associated with a limb. For instance, operating in proper alignment, operating within safety parameters, and operating without foreseeable internal failure are all examples of suitable working conditions of a device associated with a limb. When a device is not properly aligned, for instance, it is not in suitable working condition.

The term "biomechanical" as used herein refers to any mechanical characteristic or property of a device associated with the mechanics of a living body. For instance, the alignment of a device associated with a limb is a mechanical characteristic of a device associated with the mechanics of a living body. Similarly, the bending of a device associated with a limb is a biomechanical property. Measuring whether certain bending indicates delamination or otherwise deterioration of a device associated with a limb is a biomechanical measurement because the delamination will change the mechanical response of the device and thus affects the way the device will interfere with the limb. Internal and external forces, such as pressure loads, experienced by a device associated with a limb are also biomechanical characteristics of the device. Certain angles of biomechanical joints could in theory be calculated from the bending characteristics of a device and the angles are thus also regarded as biomechanical properties.

The term "predetermined" as used herein refers to any property, function, value, etc. determined at a prior period of time to application. For instance, a threshold value, algorithm, or status condition used to evaluate measurements taken on a device associated with a limb may all be predetermined. Some predetermined algorithms, conditions, values, variables, functions, etc. are used to calculate other values, etc. on the fly. Thus, a predetermined range may be understood both as a range of numbers that were selected previously (that is, that were predetermined) and as a range of numbers determined dynamically by a predetermined algorithm. The same is true of a predetermined threshold.

The phrase "user interface" as used herein means any means for perceiving the readings of the sensors of an intelligent device. For instance, a user interface may comprise an LCD monitor of a computer that is attached to an intelligent prosthetic foot. Alternatively, a user interface may be an LED indicator mounted on an intelligent prosthetic foot. In other embodiments, a user interface may comprise sound signals transmitted to the user of an intelligent foot and received through headphones. It will be appreciated that there are many ways in which the information from the sensor system may be communicated to a user or a third party. The phrase "user interface" should not be construed to be restricted to users. Thus, a trained prosthetist may be the intended user of a user interface.

A performance characteristic is any characteristic particular to the performance of a device. For instance, one example of a performance characteristic is the bending of a device, such as the bending of a prosthetic foot, an orthotic foot, or a shoe. Moreover, a performance characteristic may measure a force, more particularly a bending force. Additionally, a performance characteristic may measure a load, more particularly a bending load. A single performance characteristic, however, may be used to detect multiple conditions. For instance, a resistive strip may be used to measure the performance characteristic of bending, which may in turn be used to determine the position of the foot relative to the ground. Accordingly, a certain degree of bending of the resistive strip may indicate that the prosthetic foot in which the resistive strip is embedded is in a heel strike position, or a toe load position, or a position in-between. Thus, a performance characteristic, such as bending, may be used to measure multiple conditions, such as heel strike, toe load, or an in-between condition. Furthermore, a performance characteristic may be combined with other performance characteristics to determine a particular condition or value. For instance, two resistive strips may be aligned in a prosthetic foot to give data concerning the bending characteristic of both the left and right portions of the foot. Taken together, these measurements may be used to determine the medial/lateral moment of the prosthetic foot.

Some embodiments of the invention integrate sensors and a microcontroller to monitor the gait dynamics of a user. For example, embodiments of the invention may be used to measure the movement and/or dynamics of a device associated with a limb, such as a prosthetic or orthotic foot. In yet other embodiments of the invention, other types of devices may be used with a foot or with other limbs. For exemplifying purposes, the following will describe an embodiment of the invention including a prosthetic foot.

One embodiment of the invention includes a prosthetic foot system that provides information relating to at least one of the following:

1. The number of steps taken on the foot
2. A toe load
3. A heel load
4. Real-time information on the foot load
5. An activity index (e.g., number of steps/time*impact level)
6. Medial/lateral alignment of the foot
7. Dorsiflexion/Plantarflexion of the foot The benefits of such data sampling include information relating to at least one of the following:

1. The activity of the user (e.g., from the number of steps taken in a particular period of time).
2. Toe load and heel load may indicate if the foot selection is correct or not. For example, the system may comprise software that processes information relating to available prosthetic foot products and determines whether the current prosthetic foot is appropriately selected for the user and/or, based on such information, suggest an alternative prosthetic foot.
3. Real-time load information is beneficial during alignment processes, and an integrated load indicator (e.g., integrated into the prosthetic foot) provides for dynamic alignment based on the real-time analysis.
4. A proprietary activity index may be used to give results on increased activity caused by different adjustments or setup configurations of various types of prostheses.
5. Deflection of the prosthetic foot may be, through a force model, translated over to a force value at each end of the prosthetic foot. This allows for the measurement of toe load and heel load through a single sensor unit.
6. From monitoring the bending of the prosthetic unit, a sudden permanent change in certain bending values may indicate a failure of the device due to breakage or delamination.

FIG. 1 depicts an example of a prosthetic foot system according to one embodiment of the invention. In general, the illustrated intelligent prosthetic foot 30 may comprise many of the common elements of a prosthetic foot, such as a heel member 32, an elongated member 34, and an attachment member 36. An intelligent prosthetic foot 30 may additionally include laminating a force sensor 38, such as a variable resistor strip, into (or onto) the prosthetic foot 30. Additionally, an intelligent prosthetic foot 30 may include a microcontroller (not illustrated), which may optionally reside on the device, such as in the housing 40 illustrated in FIG. 1. In the illustrated embodiment, connecting wires 42 provide a path for communicating data to a microcontroller (not illustrated) residing in the housing 40. The illustrated intelligent prosthetic foot 30 provides a user interface 44, consisting of two LED lights, for communicating data gathered and processed.

The force sensor 38 is advantageously positioned on the prosthetic foot so as to be able to measure forces, more particularly bending forces, on both sides of a bending axis of the foot. In one embodiment of the invention, at least one sensor is positioned lengthwise (anterior/posterior direction) on the prosthetic foot. Such positioning of the sensor(s) advantageously provides for the monitoring of portions of the prosthetic foot where maximum bending is generally expected. In a further embodiment, at least one sensor is positioned lengthwise on each side of the prosthetic foot. This provides for the sensing of differences in force in the medial/lateral plane, which may be used to calculate the moment of the foot.

When the prosthetic foot bends, the resistance in the variable resistor strip changes. A microcontroller monitors the changes in resistance (such as through continuous or periodic monitoring) and detects different bending in the foot based on the changes in resistance (e.g., such as through a predetermined algorithm). In one embodiment, the microcontroller is an ATMEL Atiny15L, which may run at a frequency of 1.2 MHz. In one embodiment, the sensors and/or microcontroller may be integrated into the prosthetic foot.

In one embodiment, the interface of the system is a RS232 serial connection from the microcontroller that is connectable to any serial device over a cable or a Bluetooth connection. in other embodiments, other types of wireless technology may be used, such as infrared, WiFi®, or radio frequency (RF) technology. In other embodiments, wired technologies may be used to communicate with the microcontroller.

In one embodiment, a software program reads and interprets the data read from the prosthetic foot. A display, such as two LED's, indicates the status of the prosthetic foot system.

Figure 2:
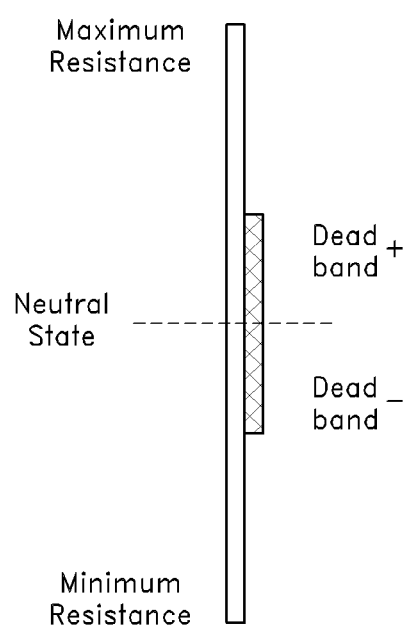
FIG. 2 illustrates certain predetermined ranges of measured resistance of a bending sensor.

Calibration of the prosthetic foot system may take place when the system is reset. That is, the "normal" state of the prosthetic foot system may be defined as the state registered when the prosthetic foot system is reset. In one embodiment, the prosthetic foot system defines a range of resistive values (or "dead zone") that is associated with a relaxed, or normal, state of the prosthetic foot. Even at this relaxed state, the prosthetic foot is generally curved and may register a particular resistive value measured through the resistive strip. Resistive values that fall outside the defined range of normal state values are generally regarded as valid state changes. For example, when the user is in stride, at the heel strike state (i.e., when the heel of the user makes contact with the ground), the resistance. (i.e., heel load value) measured through the resistive strip is generally less than the relaxed state value(s). At the toe load state (i.e., state just prior to the foot leaving the ground), the resistive value (i.e., toe load value) is generally greater than the relaxed state value(s). For a full "step" to be registered by the prosthetic foot system (e.g., incrementing a step count), the prosthetic system generally awaits a heel strike state (low resistance) and a toe load state (high resistance), which states may also occur in the reverse order (i.e., toe load state and heel strike state). FIG. 2 graphically illustrates a scale of different states (e.g., dead band) in which a measured resistive value may fall.

The following description provides an example of the above-disclosed method. A user and/or prosthetist defines a relaxed state as having a resistive value of approximately 20 kiloOhms, a heel strike state as having a resistive value of approximately 10 kiloOhms, and a toe load state as having a resistive value of approximately 40 kiloOhms. The "dead zone," therefore, includes the relaxed state value, which is greater than the heel load value, and is less than the toe load value. When a measured value from the resistive strip exceeds the "dead zone" range of values and/or the toe load value, then a TRUE value is assigned for a toe load variable. If the measured value from the resistive strip is less than the "dead zone" range of values and/or the heel load value, then a TRUE value is assigned for the heel strike variable. For each successive programming cycle, if the variables for heel strike and toe load are both TRUE, then a step counting variable is incremented by one and both the toe load and heel load variables are reset to a FALSE value. In another embodiment, only one of the heel strike and toe load variables need be TRUE for the step counting variable to be incremented. This process can continue for each step within a cycle, and the resulting information may be stored in a report and/or observed by a prosthetist for alignment, as discussed below.

The display portion of the prosthetic foot system may be used to indicate real-time information of the prosthetic foot system, and preferably the foot load. For example, if neither of the LED's of the display portion is lit then the prosthetic foot is presumably in an aligned position. On the other hand, if the prosthetic foot system experiences a force greater than an acceptable value for the toe load or heel load, the display may indicate such an overload to the user or prosthetist. For example, the display may indicate through an LED flashing pattern the type and/or magnitude of force experienced by the prosthetic foot system and/or the type of corrective alignment needed. In one embodiment, for dynamic alignment (e.g., aligning a prosthetic foot system foot based on the (current) gait properties of the user), the prosthetic foot system foot may indicate, through a LED flashing sequence of some kind, after walking that the alignment is too far posterior or anterior.

A prosthetist may use the information generated by the sensor (e.g., through the LED display or through data transmitted from the sensor) to align the prosthetic foot. For example, anterior/posterior alignment of the prosthetic foot can be performed by adjusting screws on the prosthetic foot. In one embodiment, such alignment comprises adjusting at least one of multiple (e.g., four) screws on the prosthetic foot. In other embodiments, other means of adjusting may be used. For example, the heel height of the prosthetic foot may be adjusted by pressing a button, which, in turn, changes the angle of the prosthetic foot. For example, an embodiment of the invention may include a design described in Applicant's co-pending U.S. application Ser. No. 10/742,455, filed on Dec. 18, 2003, and entitled "PROSTHETIC FOOT WITH ROCKER MEMBER," the entirety of which is hereby incorporated by reference and is to be considered as part of this specification. As the prosthetic foot is tilted downwards (plantarflexion), the toe load increases and the heel load decreases. Likewise, titling the prosthetic foot upwards (dorsiflexion) increases the heel load and decreases the toe load.

Similar types of alignment may be performed for medial/lateral alignment in a system wherein the sensor measures medial/lateral loads. This alignment may be performed based on a prosthetist's direct and/or real-time observation of the LED's provided on the device or by reviewing a report generated based on the data gathered with respect to the sensor measurements. This alignment information may also be provided to a manufacturer to provide information on how the device was treated and/or performed.

In one embodiment, a computer program analyzes the alignment information to give recommendations based on the measurements from the device. The computer program may function either in real-time or on a summary basis, and may display a computed result after some predefined walking pattern has been carried out by the user.

Figure 3:
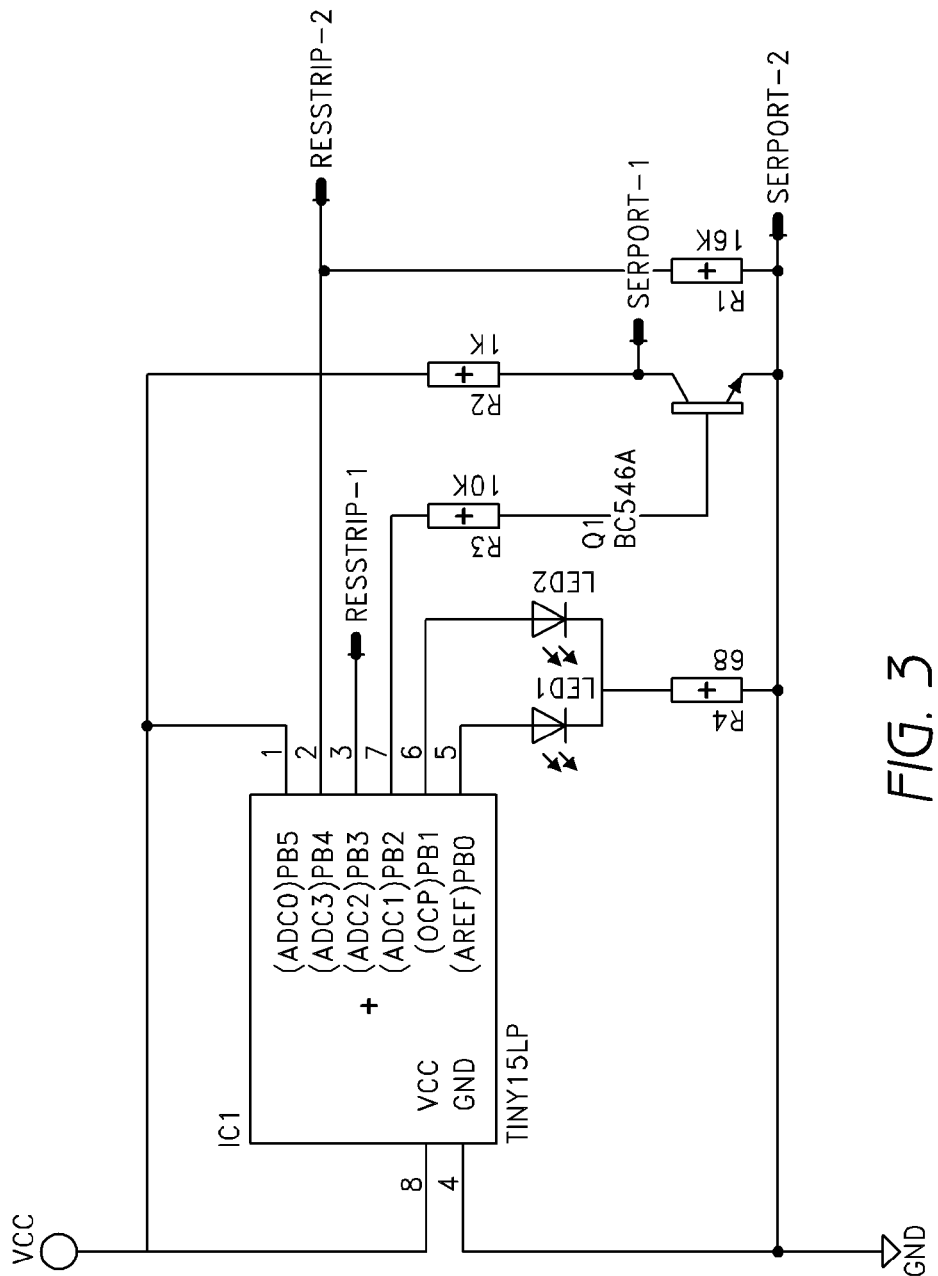
FIG. 3 illustrates a schematic diagram of certain electronic components of an intelligent device.

FIG. 3 depicts a schematic diagram of one embodiment of the prosthetic system described above. In particular, the schematic diagram shows a processor (ATMEL Atiny15L) in communication with two resistive strips (RESSTRIP-1 and RESSTRIP-2) and various other components. A corresponding part list to the schematic of FIG. 3 may be as follows:

| Part | Value | Device | Package | Library |
|---|---|---|---|---|
| IC1 | TINY15LP | TINY15LP | DIL08 | atmel |
| Q1 | BC546A | BC546A | TO92-EBC | transistor-npn |
| R1 | 16K | R-EU_0204/5 | 0204/5 | rcl |
| R2 | 1K | R-EU_0204/5 | 0204/5 | rcl |
| R3 | 10K | R-EU_0204/5 | 0204/5 | rcl |
| R4 | 68 | R-EU_0204/5 | 0204/5 | Rcl |
| RESSTRIP | | 53047-02 | 53047-02 | con-molex |
| SERPORT | | 53047-02 | 53047-02 | con-molex |
| U$1 | | LED3MM | LED3MM | Led |
| U$2 | | LED3MM | LED3MM | Led |

Figure 4:
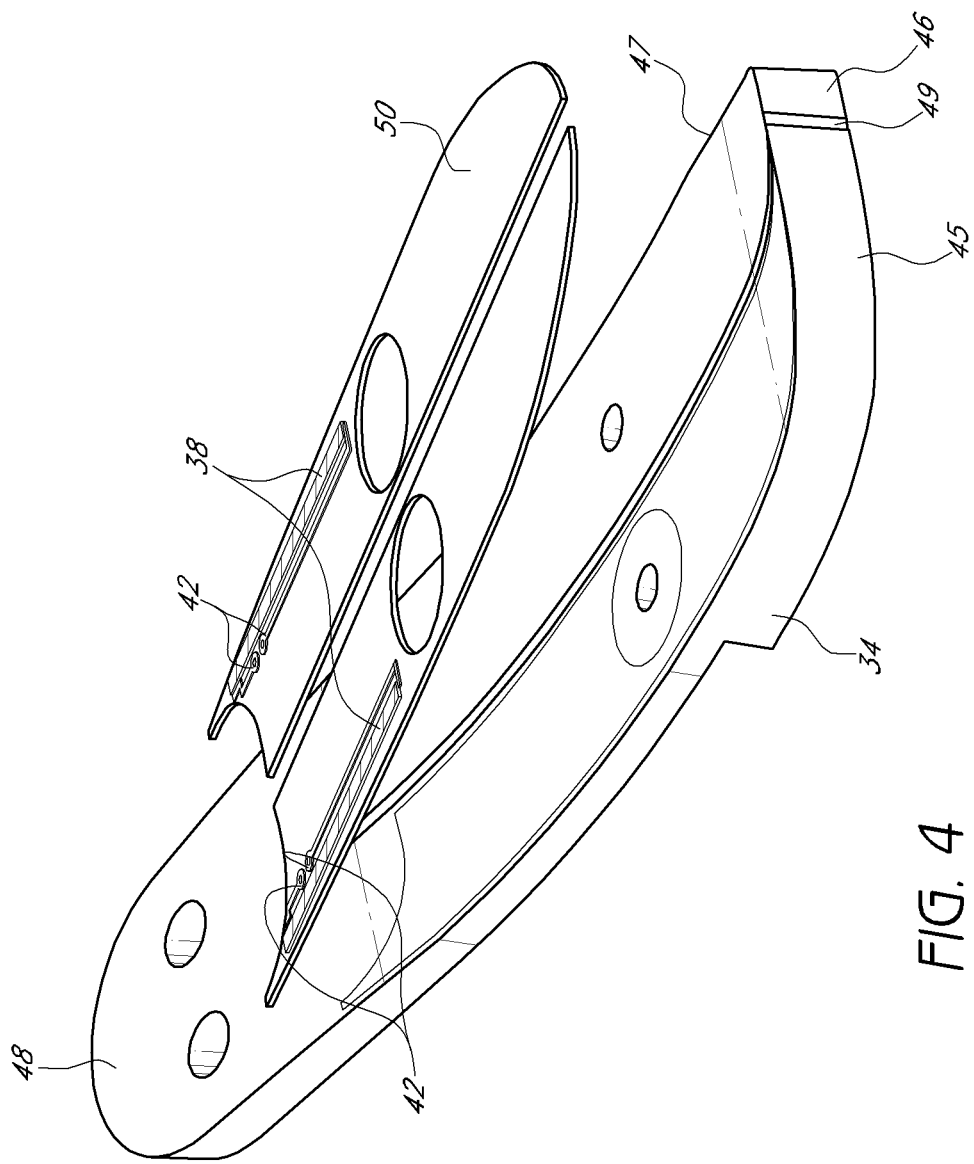
FIG. 4 illustrates a three-dimensional view of a sensor system ready for attachment to a portion of a prosthetic foot.

FIG. 4 illustrates a three-dimensional view of a sensor system ready for attachment to a portion of a prosthetic foot. The sensor system includes two bending force sensors 38 (such as variable resistor strips) ready for attachment to form an intelligent prosthetic foot 30. The prosthetic foot may be any suitable prosthetic foot where there is a portion of the foot that bends under load. For example, the following prosthetic feet available from Össur of Reykjavik, Iceland: Axia™, Ceterus®, Elation™, LP Ceterus™, Chopart, K2 Sensation™, LP Vari-Flex®, Modular III™, Re-Flex VSP™, Cheetah®, Flex-Sprint™, Flex-Run™, Talux®, Vari-Flex®, Flex-Foot® Junior, Flex-Symes™, and Sure-Flex®. Further details of certain prosthetics feet are disclosed in the following patents and applications hereby incorporated by reference in their entireties: U.S. patent application Ser. No. 10/642,125; U.S. patent application Ser. No. 10/944,436; U.S. Pat. No. 6,969,408; U.S. patent application Ser. No. 10/742,455; U.S. Pat. Nos. 6,899,737; 5,181,932; 4,822,363; 6,071,313; and 6,811,571.

Figure 6:
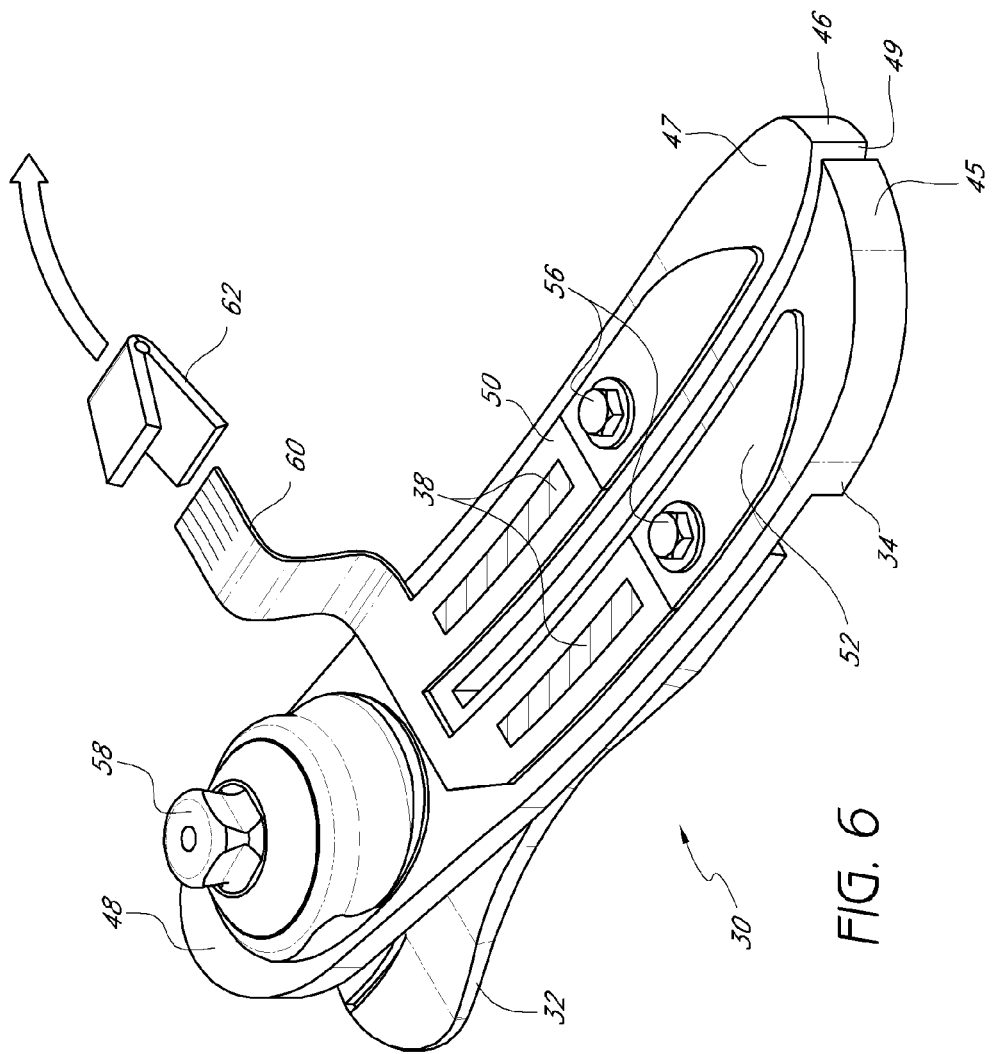
FIG. 6 illustrates a simple intelligent foot with a clip on connector for communicating data gathered from the bending sensors.

As illustrated, the foot member of the intelligent prosthetic foot 30 of FIG. 4 includes an elongated member 34 extending between a front end 47 and at a rear end 48. The foot member of the intelligent prosthetic foot 30 is preferably made from an integral piece of material which is substantially plate-like, having a substantially flat configuration with a substantially rectangular cross-section along its length. As shown in FIG. 6, the foot member further comprises a heel member 32 extending rearwardly from a location on the foot member intermediate the front end 47 and rear end 48. The heel member 32 may also have an elongate, substantially-plate like configuration like the elongated member 34. As shown in FIG. 6, the elongated member 34 and heel member 32 can be connected using bolts 56 or other suitable means. An adapter 58 is provided on an upper surface of the foot member for connection to a pylon or other intermediate member.

The elongated member 34 and heel member 32 are preferably constructed of a resilient material that is capable of flexing in multiple directions. The material may comprise multiple layers, or laminae. Examples of possible materials for the members are carbon, any polymer material, and any composite of polymer and fiber. The polymer could be thermoset or thermoplastic. In a composite, the fiber reinforcement could be any type of fiber, such as carbon, glass or aramid. The fibers could be long and unidirectional, or they could be chopped and randomly oriented.

The elongated member 34 as illustrated in FIG. 4 is split into multiple independent toe members configured to flex substantially independently of one another at least partially along their length. In the illustrated embodiment, the elongated member 34 is split into two independent toe members 45, 46. For example, the foot member 10 may comprise at least one longitudinal slot 49 having a substantially constant width extending from the front end 47 thereof towards a rear point proximal the rear end 48 of the elongated member 34.

Further details of a base prosthetic foot may be found in U.S. patent application Ser. No. 10/642,125, incorporated by reference herein.

In FIGS. 5 through 10 the same reference numbers refer to similar features common to both figures. Additionally, the text below refers to a component called a "sensor system." The sensor system should be understood to mean any collection of bending force sensors in accordance with the embodiments of the invention. In the illustrated embodiments in FIGS. 5 through 10, the sensor system 50 comprises two bending force sensors 38. In addition to the sensors, the phrase "sensor system" refers to the substrate upon which the sensors are embedded, which substrate may be, for example, attached, bonded, embedded, adhered, laminated, combinations of the same and the like, etc. to a device associated with a limb, such as a prosthetic foot. Additionally, the sensor system illustrated in FIG. 5 comprises connecting wires 42 that provide the path for sensed data to reach some processing unit, not generally to be considered part of the sensing system. The illustrated sensor system 50 also includes an attachment portion 52 without any sensor material. The illustrated attachment portion 52 provides additional surface area for adhering the sensor system 50 to, for instance, a prosthetic foot. In other embodiments, the sensor system 50 may be laminated into the fibers of an intelligent device, such as the carbon fibers of a prosthetic foot. The holes 54 provide an entry for the bolts, for example the bolts 56 as illustrated FIG. 6, that are used to adjoin plates of the prosthetic foot. The connecting wires 55 provide a communication path from the bending force sensors 38 to a connecting attachment that provides a communication path to a computing device that processes the data.

Figure 5:
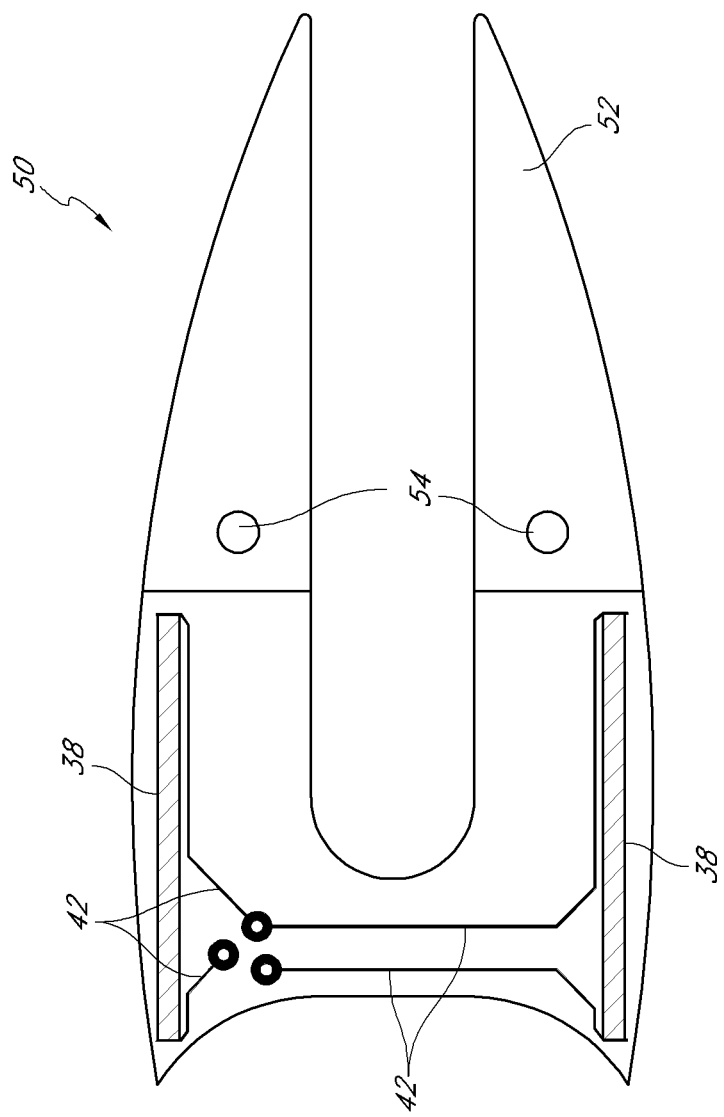
FIG. 5 illustrates a sensor system with two bending force sensors.

The sensor system 50 shown in FIG. 5 includes two elongate sensors 38, which may be resistive strips such as described above. It will be appreciated that any suitable sensor may be used to measure a desired performance, force, alignment, or biomechanical characteristic of the foot. Such sensors 38 comprise an elongate, substantially planar body that provides a flat surface that extends across an upper surface of the prosthetic foot in a longitudinal or posterior-to-anterior direction. As used herein, the elongate configuration of the sensors 38 generally refer to the sensors having a length to width ratio of greater than about 2:1, more preferably greater than about 5:1 or even 10:1. In one embodiment, the sensors 38 have a length of about ½ inch or greater, more preferably about one inch or greater, more preferably about two inches or greater, or even about three inches or greater. The width of the sensors 38 may in one embodiment be between about ⅛ of an inch and ½ inch. The sensors 38 also have a flexible construction, allowing them to bend with the foot member during use of the foot. Some sensors may comprise resistive carbon technology. Suitable sensors are available from Spectra Symbol Corp. of Salt Lake City, Utah.

As illustrated in FIG. 6, the sensors 38 are preferably located along an intermediate portion of an upper surface of the foot member. However, it will be appreciated that the sensors 38 may be provided at any suitable location for taking bending or other measurements. The sensor system 50 as illustrated is provided such that left and right sensors 38 are provided on opposite sides of the slot 49, such that measurements can be taken not only for bending along an anterior-posterior direction, but also comparisons can be made for medial/lateral differences.

Because FIGS. 6 through 10 contain many similar elements previously described, the description of those elements is not repeated.

FIG. 6 illustrates a simple intelligent foot with a clip on connector for communicating data gathered from the bending sensors. In the illustrated embodiment, the sensor system 50 is adhered to the top surface of a prosthetic foot. In this simple embodiment, the intelligent foot does not perform any processing. Instead, the connecting wires providing a path for the sensed data are configured into a connecting band 60 to which a simple clip-on connector 62 may be attached. The clip-on connector 62 provides paths for the sensed data, leading to a connectible processing component, such as those discussed below. In this embodiment, the processing, storing, and outputting of sensed data occurs on a connectible device (not illustrated). Such an external processing component may be adapted to perform functions as described below. Because the sensor system (comprising bending force sensors) is cost effective, the sensor system 50 may be included with many devices associated with limbs, for instance prosthetic feet. The sensor system 50 may remain permanently attached to a prosthetic foot. The sensor system 50 might be connected to a processing device when the prosthetic foot is first fitted to its user and thereafter during successive visits to, for instance, a trained prosthetist.

Figure 7:
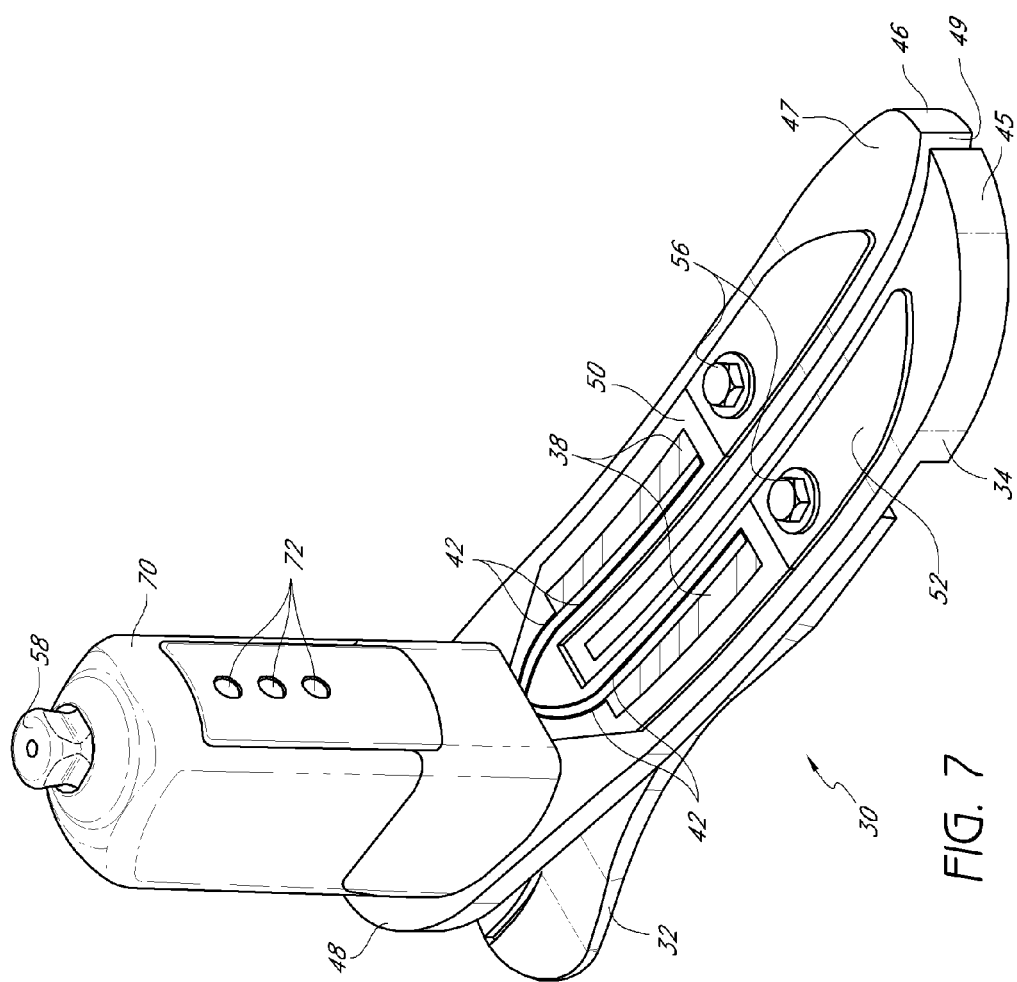
FIG. 7 illustrates an intelligent prosthetic foot with a built-in component for processing and displaying the data gathered from the bending sensors.

FIG. 7 illustrates an intelligent prosthetic foot with a built-in component for processing and displaying the data gathered from the bending sensors. In contrast to the embodiment illustrated in FIG. 6, the embodiment illustrated in FIG. 7 comprises a built-in processing unit 70, which might include a processor (not illustrated) for processing the sensed data, a battery (not illustrated) for operating the built-in processing unit 70, and a user interface 72 comprising three LED lights. These lights might be configured so as to indicate when the prosthetic foot is experiencing, respectively, a heel strike, a toe load, or a neutral position in between. Additionally, the lights may indicate when heel strike or toe load values are inside or outside of a predetermined or a desired range or exceed a threshold value. A trained prosthetist might observe the lights while, for instance, aligning the prosthetic foot for its user. Such alignment might occur while the user is, for example, standing, sitting, walking, or running, thereby providing for either static or dynamic alignment.

Additionally or alternatively, the built-in processing unit 70 might comprise a sophisticated digital signal processor, capable of indicating that, for instance, gait is not optimal. In this instance, the lights on the user interface 72 might indicate certain non-optimal performance characteristics. In some embodiments, the built-in processing unit 70 might be configured to determine other conditions related to, for instance, a user's safety, usage statistics, selection of device, or internal failure of the device. For instance, the processor might be programmed to detect if a prosthetic foot is too stiff. This condition may be detected if the sensor system never detects a certain amount of bending beyond a predetermined or desired threshold (e.g., a desired threshold previously defined by fixed values or algorithms). Other detected safety conditions might include an increase in weight of the user, a predominant favoring of one side of the prosthetic foot, or irregularities in detecting alternating heel strikes and/or toe loads. An example of the kind of internal failure that might be detected is the delamination of the carbon fibers of, for example, a prosthetic foot. The built-in processing unit might detect that the device is bending too much, for instance, by sensing that a predetermined threshold has been exceeded. Too much bending may be indicative of delamination of the carbon fibers, which may lead to the toe breaking off if left unattended. The user interface 72 might be programmed to signal delamination, as well as other detected safety and/or internal failure conditions. The built-in processing unit 70 might also be configured for vibration analysis corresponding to changes in frequency and/or resonation.

In some embodiments, the built-in processing unit 70 comprises random access memory (RAM) embedded in the processor. This memory may be used during the real-time processing of the sensed data. Additionally or alternatively, the built-in processing unit 70 may comprise long-term memory, such as flash memory, for storing accumulated data, such as the number of steps, force, load, or bending measurements, including step-by-step measurements. This stored data may be used to calculate an activity index such as described above. In these embodiments, the processor would be able to provide feedback based on the history of gait dynamics detected by the sensor system 50. Threshold values might be stored in the long-term memory or embedded in the control logic of the processor.

Figure 8:
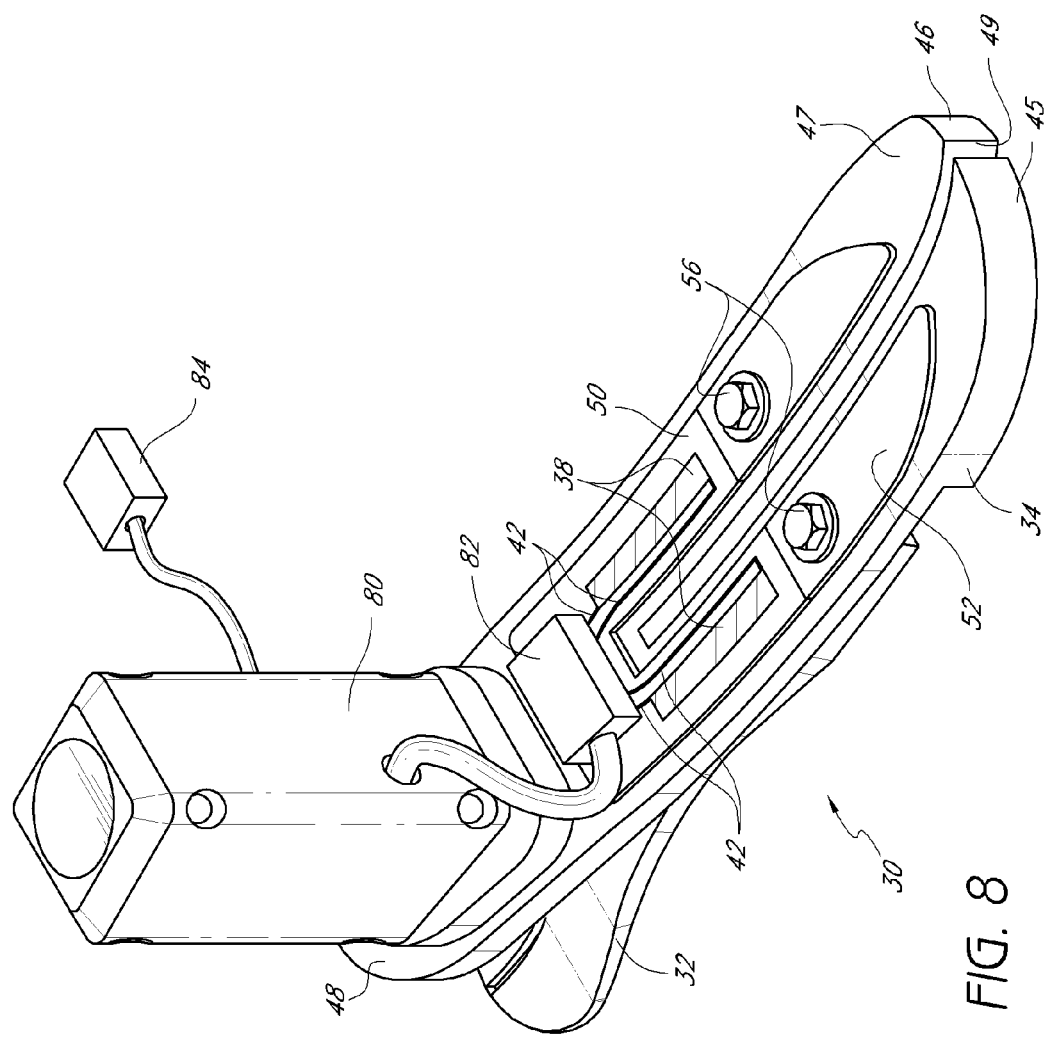
FIG. 8 illustrates an intelligent prosthetic foot with detachable component for processing data gathered from the bending sensors.

FIG. 8 illustrates an intelligent prosthetic foot with detachable component for processing data gathered from the bending sensors. In this embodiment, the sensor system 50 is linked to a detachable processing unit 80 through a snap-on connector 82. The detachable processing unit might perform all of the functions attributed to the built-in processing unit, described above with reference to FIG. 7. Additionally, the detachable unit 82 may be configured to interact with another computing/peripheral device through the alternative connector 84. The other computing/peripheral device might provide additional processing or might provide a user interface. In some embodiments, the detachable processing unit 80 may comprise primarily a memory for storing the sensed data, which is processed by another device either through the alternative connector 84 or some other connection (not illustrated).

Figure 9:
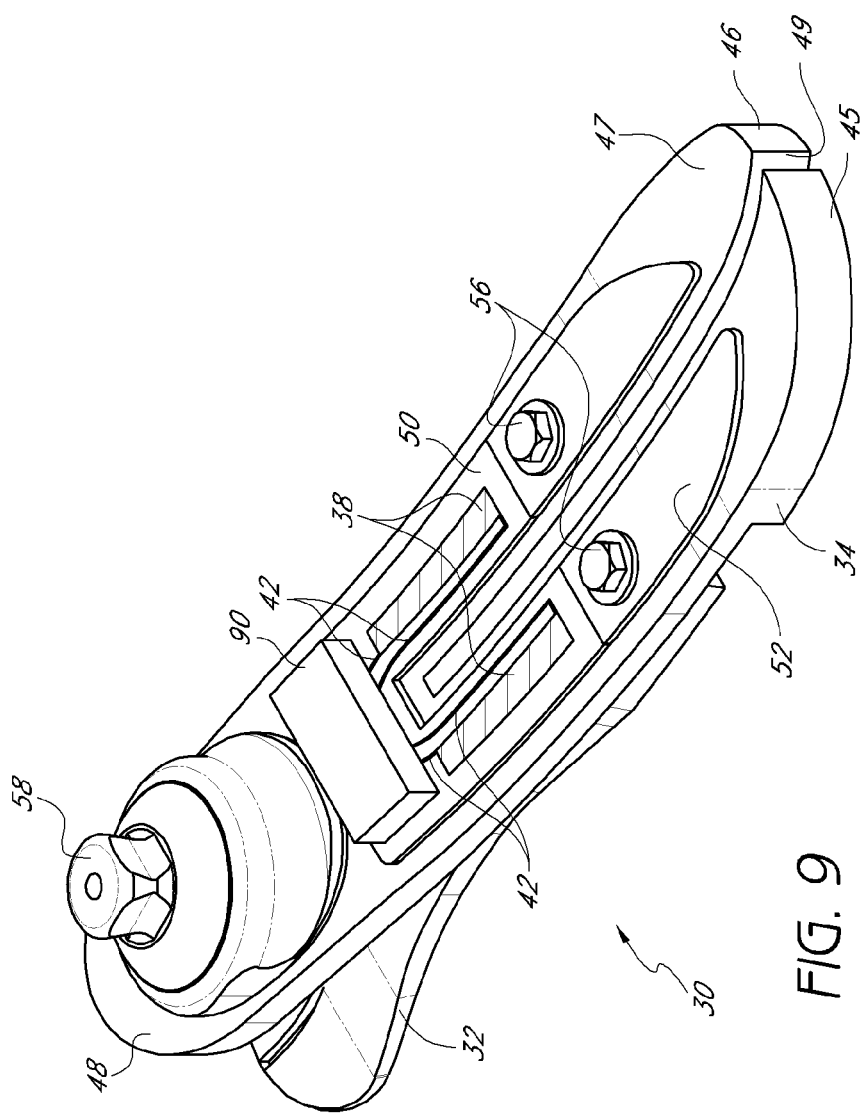
FIG. 9 illustrates an intelligent prosthetic foot with a wireless unit for communicating data gathered from the bending sensors.

FIG. 9 illustrates an intelligent prosthetic foot with a wireless unit for communicating data gathered from the bending sensors. In this embodiment, the sensor system 50 communicates the sensed data to a remote processing unit (not illustrated) via a wireless transmitter 90.

Figure 10:
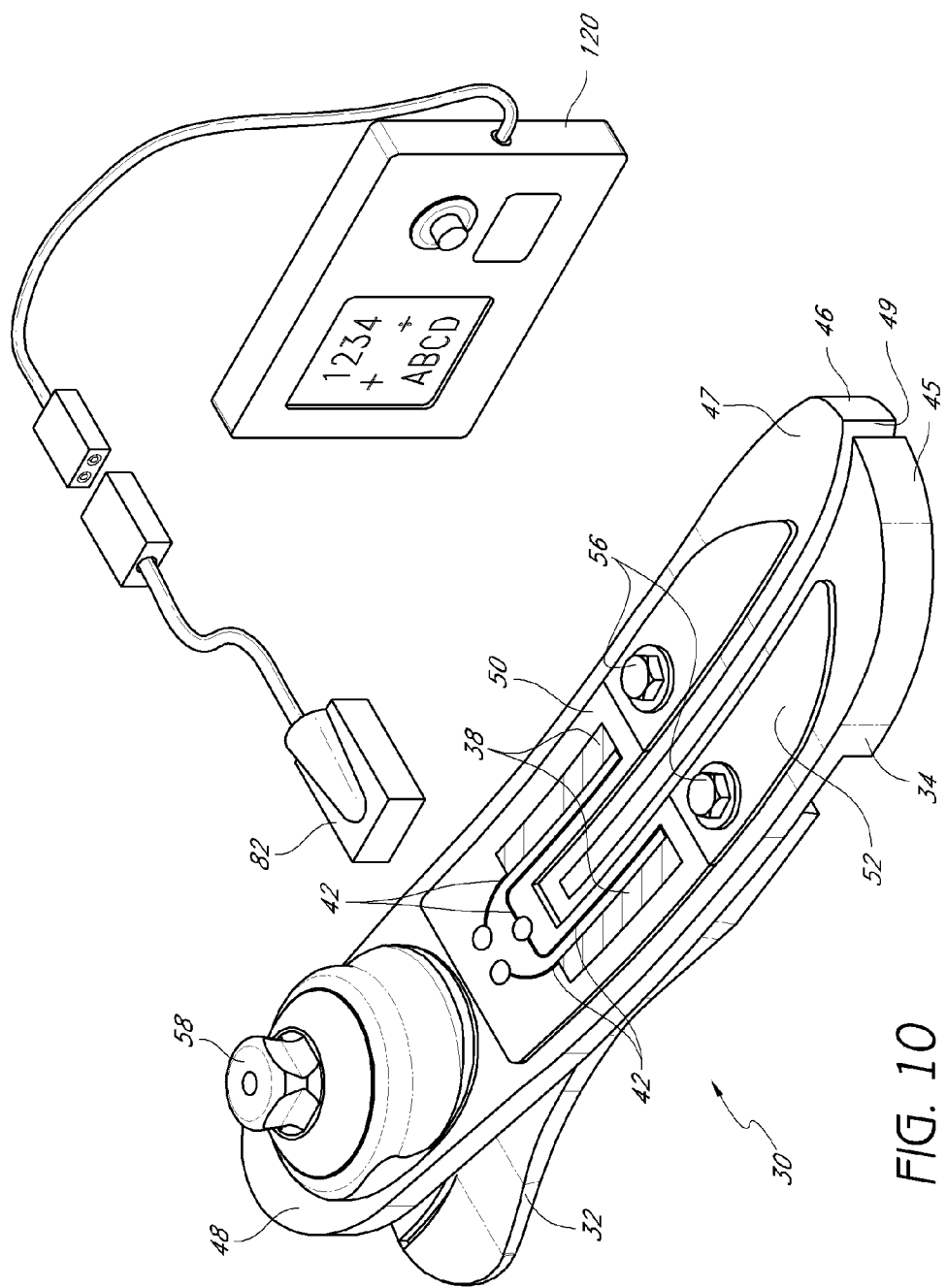
FIG. 10 illustrates an intelligent foot with a snap-on connector for connecting a computing device that processes and displays the data gathered from the bending sensors.

As discussed with reference to FIG. 6 or to FIG. 8, in some embodiments, the intelligent foot might be connected to another computing/peripheral device for processing and/or user interface functionality. FIG. 10 illustrates an intelligent foot with a snap-on connector for connecting to other computing/peripheral devices. In contrast to the embodiment illustrated in FIG. 8, the embodiment illustrated in FIG. 10 does not have a local processing unit, but communicates all data to a separate computing/peripheral device. With reference to FIG. 10, the sensor system 50 is connected through a snap-on connector 82 to a dedicated computing device 120, which might also be a personal digital assistant (PDA). FIGS. 11 through 14 illustrate possible computing/peripheral devices, including, respectively, a wristwatch 110 (FIG. 11), a dedicated computing device 120 (FIG. 12), a laptop 130 (FIG. 13), and a set of headphones 140 (FIG. 14). One skilled in the art will appreciate that there are many computing/peripheral devices that may be adapted to provide supplementary or complementary processing and/or interface functionality, which should be considered as contemplated by and included in the embodiments described above.

As illustrated in FIG. 14, a user of an intelligent device may configure the device to transmit sound signals received by a user's headphones or earphones. These sound signals might help the user to associate certain sounds with the detected performance characteristic perceived by a sensor system. In one embodiment, the performance characteristic is the bending of a resistive strip, which may indicate, alternatively, a heel strike state and a toe load state of a prosthetic foot. The intelligent device may be configured to give sound signals for these alternating events during the movement of the device. For example, the user of the intelligent foot may train with the device on a periodic basis in order to train the brain to associate pressure on the amputated limb, for instance, with the performance characteristics perceived by wearing the intelligent device. For example, the user may feel certain pressures on the amputated limb from the device, or an intermediate member such as a pylon, at the moment of a heel strike. At this moment, the intelligent device may be configured to transmit a particular sound signal. Over time, the user may learn to associate the sound of a heel strike with the related pressures felt on the limb. Another sound may indicate when the sensor system has perceived a toe load. Thus, when the user hears this alternative sound, the user's brain may begin to associate that sound with the different pressure sensations felt on the amputated limb, caused, for instance, by the contact with the socket of a prosthetic foot. When the intelligent device detects neither a heel strike nor a toe load, for example, the intelligent device may emit another sound, indicating that there is no perceived state. By training the user to associate sounds with, for instance, the pressure on a limb caused by a device associated with a limb, the user of the device may begin to rehabilitate the natural proprioceptive functions of the limb, which may be impaired. In this sense, embodiments of the invention may be used to provide artificial proprioception to a user of the device.

In some embodiments, the intelligent device may emit a constant and continuous sound, indicating the present state being perceived by the sensor system. In other embodiments, different discrete sounds may be used. In addition to the rhythm, the pitch and volume may also be varied, as well as any other adjustment that would affect the sound heard by the user or another individual. As the user wears the intelligent device, the particular gait pattern, for example, of the user will be represented by the sounds emitted from the intelligent device, such as a prosthetic foot in accordance with embodiments of the invention. Over time, the user may become accustomed to the alternating sounds and begin to recognize and associate different feelings from the device through the predetermined sounds (e.g., the programmed sounds assigned to different sensing readings). Over a period of time, the user may become accustomed to the sounds and associated feelings, such that the user no longer needs the sounds in order to interpret the feelings from, for example, the prosthetic socket. Thus, in some embodiments, the audio signals may be configured on a temporary basis. In these embodiments, the audio function may consist of a connection to the sensor system, a processor for receiving sensor inputs and a transmitter for creating sound signals for the associated performance characteristics. These components may be provided on a detachable component to the device, or may be wirelessly connected. In other embodiments, the intelligent foot may come equipped with the transmitting unit. In other embodiments, the sound transmitting unit may be attached to the foot as a separate computing device, such as a portable, laptop, or desktop computer. The user may receive the auditory signals through a variety of devices. For instance, as already mentioned, the user may wear headphones that receive the signals. These signals may be transmitted either through wireless or wired communication devices. For instance, the wireless signals may be transmitted through a Bluetooth, WiFi®, infrared, or radio transmitting device. The headphones may be worn in or over the user's ear or possibly implanted within the ear. In other embodiments, the sound may be emitted a speaker on the device that broadcasts sound to any within earshot.

Embodiments of the present invention relate to, or may be used in combination with, the subject matter disclosed in the following applications, each of which is hereby incorporated herein by reference: U.S. patent application Ser. No. 11/056,344, entitled "SYSTEM AND METHOD FOR MOTION-CONTROLLED FOOT UNIT," filed on Feb. 11, 2005, and published on Sep. 8, 2005, as U.S. Patent Application Publication No. 2005/0197717-A1; U.S. patent application Ser. No. 11/057,391, entitled "SYSTEM AND METHOD FOR MOTION-CONTROLLED FOOT UNIT," filed on Feb. 11, 2005, and published on Sep. 1, 2005, as U.S. Patent Application Publication No. 2005/0192677-A1; U.S. patent application Ser. No. 11/315,648, entitled "SYSTEMS AND METHODS FOR LIMB DETECTION," filed on Dec. 22, 2005; U.S. patent application Ser. No. 11/077,177, entitled "CONTROL SYSTEM AND METHOD FOR A PROSTHETIC KNEE," filed on Mar. 9, 2005, and published on Dec. 22, 2005 as U.S. Patent Application Publication No. 2005/0283257-A1; U.S. patent application Ser. No. 11/123,870, entitled "MAGNETORHEOLOGICALLY ACTUATED PROSTHETIC KNEE," filed on May 6, 2005; U.S. patent application Ser. No. 10/615,336, entitled "SOCKET LINER INCORPORATING SENSORS TO MONITOR AMPUTEE PROGRESS," filed Jul. 8, 2003, and published on Mar. 25, 2004, as U.S. Patent Application Publication No. 2004/0059432; U.S. Pat. Nos. 6,610,101; and 6,764,520.

It will be understood that the foregoing is only illustrative of the principles of the invention, and that various modifications, alterations, and combinations can be made by those skilled in the art without departing from the scope and spirit of the invention. Although this invention has been described in terms of certain embodiments, other embodiments that are apparent to those of ordinary skill in the art, including embodiments which do not provide all of the benefits and features set forth herein, are also within the scope of this invention. Accordingly, the scope of the present invention is defined only by reference to the appended claims.

What is claimed is:

1. A method of using a prosthetic foot system, comprising:
obtaining data from a sensor system provided on a prosthetic foot system and used to measure a characteristic of a prosthetic foot system while in use;
processing the data with a processor to determine a condition of the prosthetic foot system; and
providing a recommendation regarding alignment of the prosthetic foot system based on the condition of the prosthetic foot system.

2. The method of claim 1, wherein the processor is configured to determine a condition of the prosthetic foot system by determining whether the data is inside or outside of a predetermined range or exceeds a threshold value.

3. The method of claim 1, further comprising compiling a history of gait information of the prosthetic foot system within a memory.

4. The method of claim 1, comprising obtaining data from a sensor system used to measure a force characteristic of the prosthetic foot system while in use.

5. The method of claim 1, wherein providing a recommendation regarding alignment comprises displaying the recommendations on a display.

6. The method of claim 1, wherein the processor is a remote processing unit from the prosthetic foot system.

7. The method of claim 1, wherein the data is obtained from the sensor system via a wireless transmitter.

8. The method of claim 1, wherein the data is obtained from the sensor system by attaching a connector to the sensor system to extract the data.

9. The method of claim 8, comprising attaching a snap-on connector to the sensor system.

10. The method of claim 8, comprising connecting the sensor system to a detachable processing unit.

11. The method of claim 1, further comprising aligning the prosthetic foot system based on the recommendation.

12. The method of claim 1, wherein the recommendation is provided in real-time as a user is using the prosthetic foot system.

13. The method of claim 1, wherein the recommendation is provided on a summary basis after a walking pattern has been carried out by a user.

14. A system for gathering information regarding a prosthetic foot, comprising:
a sensor system configured to be placed on a prosthetic foot, the sensor system comprising at least one sensor configured to measure a performance characteristic of the prosthetic foot;
a processor configured to process data from the at least one sensor to determine a condition of the prosthetic foot;
a connector configured to communicate with an external computing device; and
a user interface configured to provide recommendations regarding alignment of the prosthetic foot system based on the data.

15. The system of claim 14, wherein the processor is configured to be coupled to the prosthetic foot and the connector is configured to communicate data from the processor to the external computing device.

16. The system of claim 14, wherein the processor is a remote processing unit, and the connector is configured to communicate data from the sensor system to the processor.

17. The system of claim 14, further comprising a memory configured to store information gathered by the at least one sensor to compile a history of bending of the prosthetic foot while in use.

18. The system of claim 14, wherein the connector provides for wireless communication with the external computing device.

19. The system of claim 14, wherein the connector provides for wired communication with the external computing device.

20. The system of claim 14, wherein the performance characteristic comprises a bending force measurement.

* * * * *